US010814066B2

(12) United States Patent
Moser et al.

(10) Patent No.: US 10,814,066 B2
(45) Date of Patent: Oct. 27, 2020

(54) MEDICATION DISPENSING APPARATUS WITH SUB-DOSE PREVENTION

(71) Applicant: Ypsomed AG, Burgdorf (CH)

(72) Inventors: Ulrich Moser, Heimiswil (CH); Christian Schrul, Burgdorf (CH); Jürg Hirschel, Bern (CH)

(73) Assignee: Ypsomed AG, Burgdorf (CH)

( * ) Notice: Subject to any disclaimer, the term of this patent is extended or adjusted under 35 U.S.C. 154(b) by 711 days.

(21) Appl. No.: 15/481,142

(22) Filed: Apr. 6, 2017

(65) Prior Publication Data

US 2017/0209651 A1 Jul. 27, 2017

Related U.S. Application Data

(63) Continuation of application No. PCT/CH2015/000138, filed on Sep. 17, 2015.

(30) Foreign Application Priority Data

Oct. 9, 2014 (EP) .................................. 14 188 326

(51) Int. Cl.
*A61M 5/315* (2006.01)
*A61M 5/24* (2006.01)
*A61M 5/31* (2006.01)

(52) U.S. Cl.
CPC .......... *A61M 5/31541* (2013.01); *A61M 5/24* (2013.01); *A61M 5/3157* (2013.01);
(Continued)

(58) Field of Classification Search
CPC .......... A61M 5/31535; A61M 5/31561; A61M 5/31585; A61M 5/31551; A61M 5/31541;
(Continued)

(56) References Cited

U.S. PATENT DOCUMENTS

2008/0306445 A1* 12/2008 Burren .............. A61M 5/31553
604/136
2013/0296802 A1* 11/2013 Moore .................... A61M 5/24
604/246

FOREIGN PATENT DOCUMENTS

CH 707217 A2 4/2014
CN 103260674 A 8/2013
(Continued)

OTHER PUBLICATIONS

International Search Report dated Dec. 1, 2015, for PCT Application No. PCT/CH2015/000138, 3 pages.
(Continued)

*Primary Examiner* — Laura A Bouchelle
*Assistant Examiner* — Justin L Zamory
(74) *Attorney, Agent, or Firm* — Dorsey & Whitney LLP

(57) ABSTRACT

Medication dispensing apparatuses for dosing-up and delivering a pre-set dosage of a fluid product include a housing; a dosing element moveable relative to the housing between a starting position and a dosed-up position; a drive system coupled to the dosing element operable to initiate or perform a dispensing operation; and a sub-dose preventing system for preventing or blocking a dispensing operation of the drive system when the dosing element has not reached the dosed-up position and for allowing or unblocking a dispensing operation of the drive system when or after the dosing element has reached the dosed-up position, wherein the sub-dose preventing system is operable to block a rotational movement in a circumferential direction of the medication dispensing apparatus of a drive element of the drive system corresponding to a dispensing direction or a dial-down direction when preventing or blocking the dispensing operation of the drive system.

17 Claims, 10 Drawing Sheets

(52) U.S. Cl.
CPC ...... *A61M 5/3158* (2013.01); *A61M 5/31535* (2013.01); *A61M 5/31536* (2013.01); *A61M 5/31548* (2013.01); *A61M 5/31555* (2013.01); *A61M 2005/2407* (2013.01); *A61M 2005/2492* (2013.01); *A61M 2005/3126* (2013.01); *A61M 2205/581* (2013.01)

(58) Field of Classification Search
CPC .......... A61M 5/31536; A61M 5/31548; A61M 5/31555; A61M 5/3157; A61M 5/3158
See application file for complete search history.

(56) References Cited

FOREIGN PATENT DOCUMENTS

| | | |
|---|---|---|
| CN | 103260675 A | 8/2013 |
| EP | 2404633 A1 | 1/2012 |
| WO | 2005097233 A1 | 10/2005 |
| WO | 2005097240 A1 | 10/2005 |
| WO | 2006125329 A1 | 11/2006 |
| WO | 2008019517 A1 | 2/2008 |
| WO | 2008148539 A1 | 12/2008 |
| WO | 2012049139 A1 | 4/2012 |

OTHER PUBLICATIONS

International Preliminary Report on Patentability dated Apr. 11, 2017, for PCT Application No. PCT/CH2015/000138, 11 pages.

\* cited by examiner

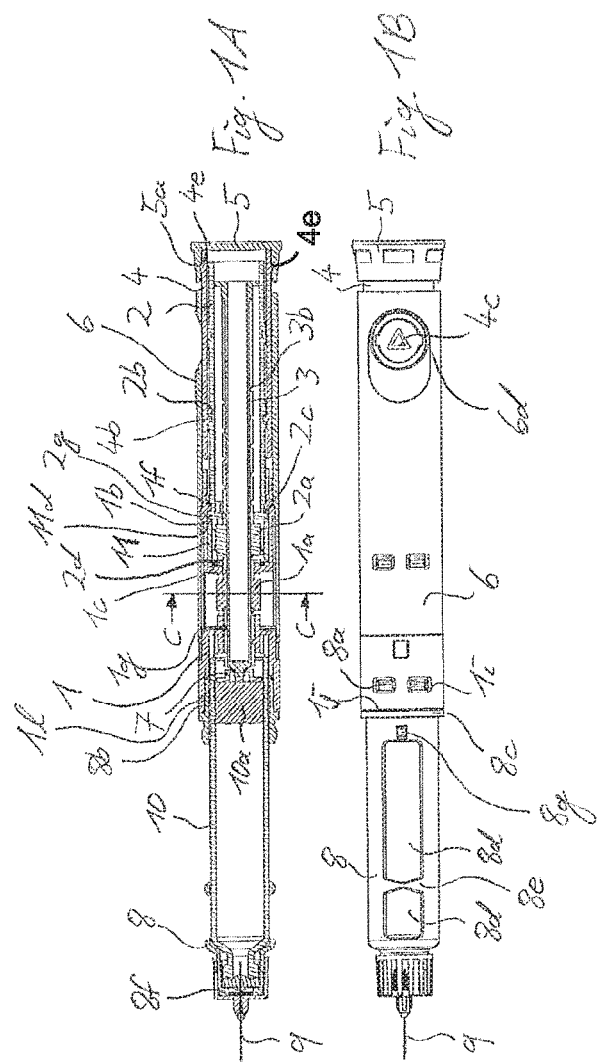

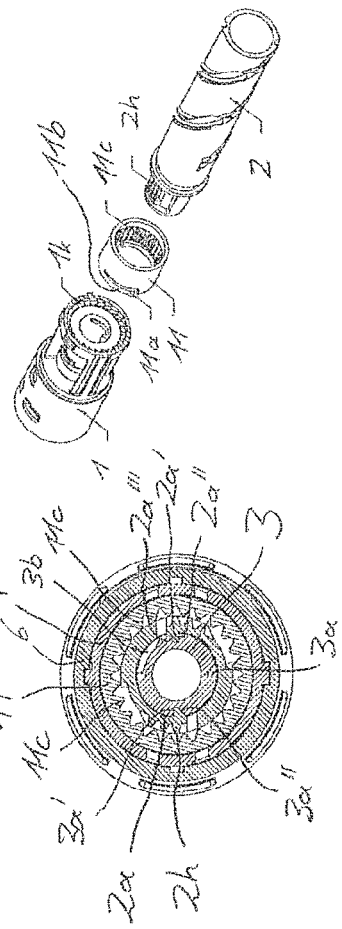

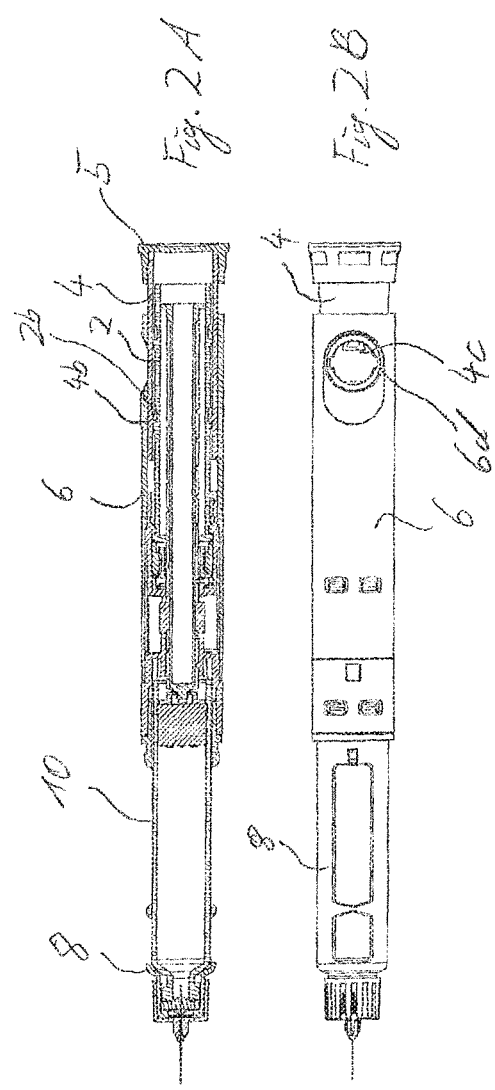

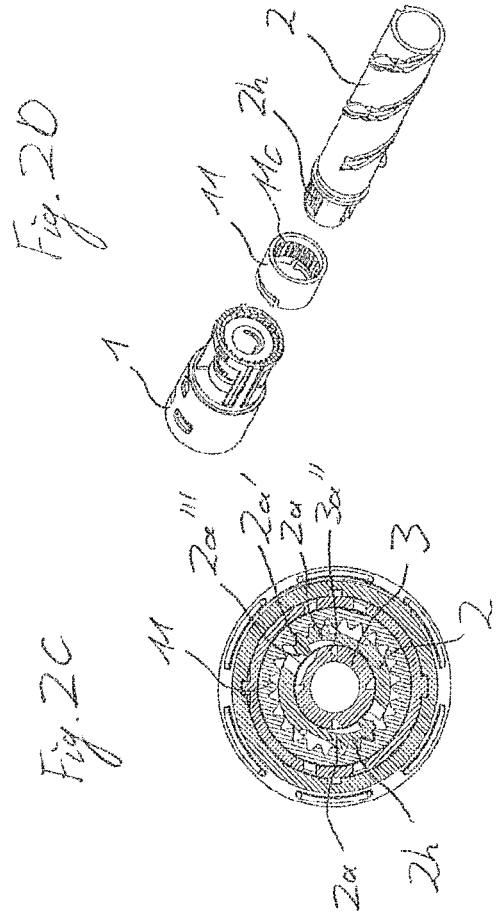

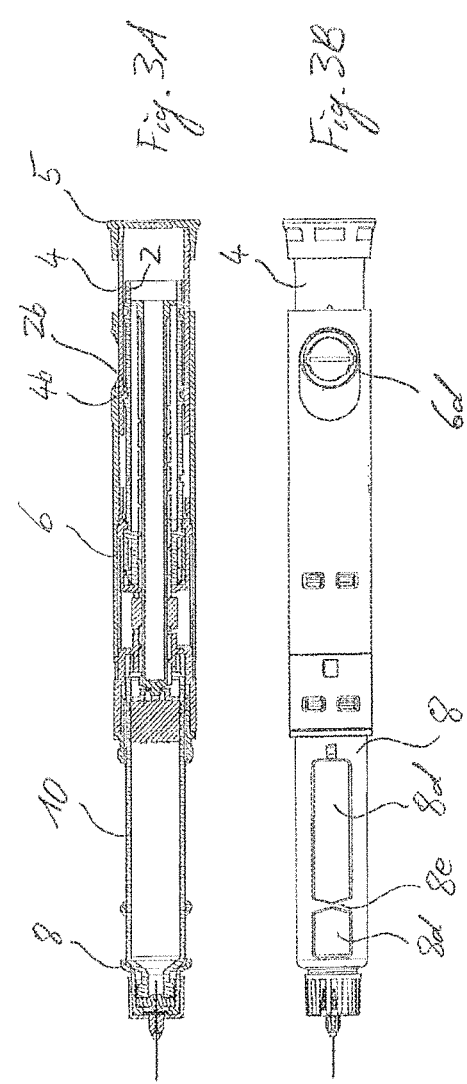

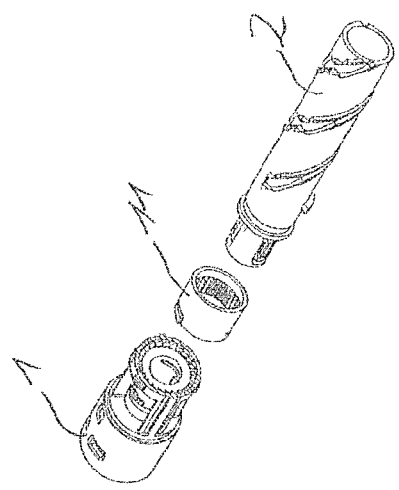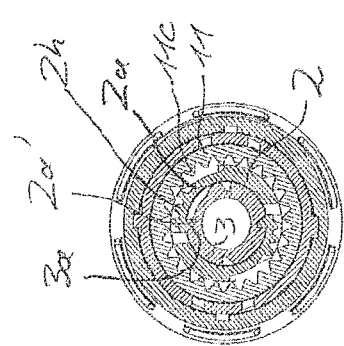

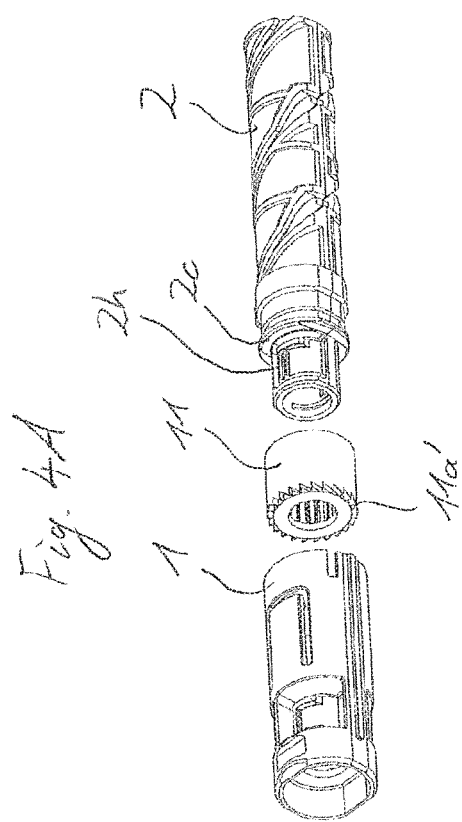

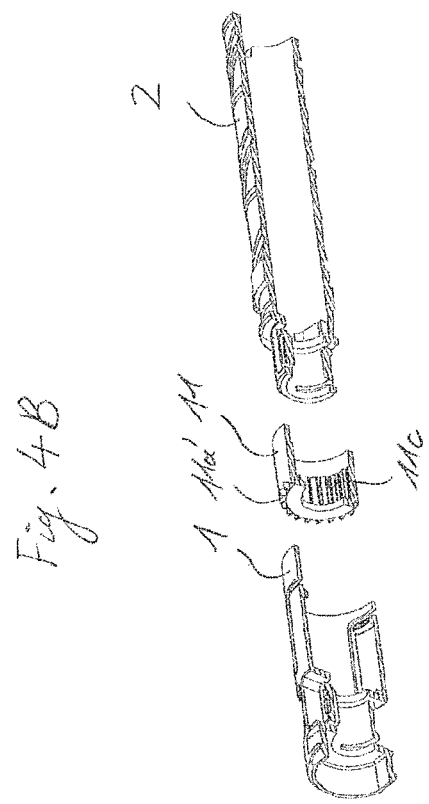

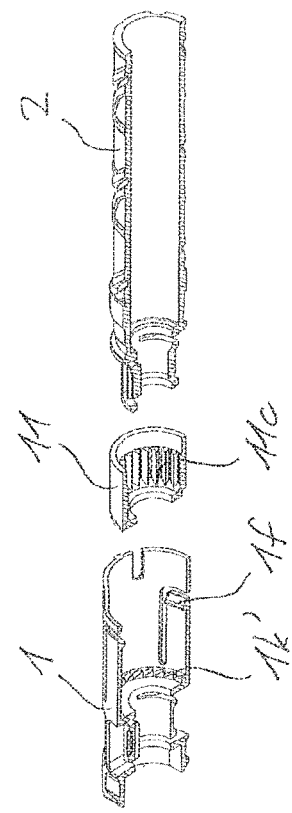

MEDICATION DISPENSING APPARATUS WITH SUB-DOSE PREVENTION

CROSS-REFERENCE TO RELATED APPLICATIONS

This application is a continuation of International Application No. PCT/CH2015/00138 filed Sep. 17, 2015, which claims priority to European Application No. 14188326.4 filed Oct. 9, 2014, the contents of all of which are herein incorporated by reference.

BACKGROUND

The present invention relates to an injection device or medication dispensing apparatus for administering a fluid product, in particular a medicament such as for example insulin or teriparatide for treating osteoporosis, and to a method for operating the device.

The term "medicament" includes any flowable medical formulation suitable for controlled administration though a means such as, for example, a cannula or a hollow needle and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

WO 2006/125 329 A1 discloses a dosing device of an injection apparatus, using which a dosage to be dispensed can be variably set. The dosing device comprises a rotating sleeve which can be rotated out of the dosing device relative to a housing of the injection device in order to prepare a dosage to be dispensed.

WO 2008/019 517 A1 discloses a fixed-dosage injection apparatus, wherein a dosage to be dispensed can be set just by rotating the end cap.

CH 707 217 A2 discloses an injection device for dosing-up and delivering a defined dosage of a fluid product, comprising a threaded plunger rod, wherein the thread comprises a toothing. The injection device also comprises a rotating sleeve and a guiding sleeve, wherein the rotating sleeve and the guiding sleeve comprise each an engaging element, which can engage with the toothing of the plunger rod. A number of engaging elements can also be arranged on the rotating sleeve and on the guiding sleeve and engage with the toothing of the plunger rod. The dosage sleeve can be in a threaded engagement with the rotating sleeve. The threaded engagement is preferably embodied as a threaded connection which is not self-locking. The rotating sleeve and the guiding sleeve can also be arranged such that they are axially fixed but can be rotated relative to each other. The rotating sleeve can also be arranged such that it can be rotated relative to the guiding sleeve and/or the dosage sleeve and/or plunger rod.

WO 2008/148539 A1 discloses an injection device having a control element that can be moved relative to an injection device for filling the injection device; a filling element coupled to the control element that can be held by a holding device or engage with or snap into the injection device after a prescribed filling motion; and having a spring element connected to the filling element and the injection device or a housing thereof, such that the filling element can be returned by the spring element, if the filling element is not moved far enough out of the injection device such that the holding device snaps in or engages.

WO 2005/097240 A1 discloses a medication dispensing apparatus having a gear set to provide a mechanical advantage to the plunging of the apparatus plunger. The gear set has a first pinion in meshed engagement with a rack of the plunger, and a second pinion in meshed engagement with a rack of a drive member of the apparatus. The gear set operatively interconnects the plunger and the drive member such that after the plunger is moved relative to the housing in a proximal direction to prepare the apparatus for injection, the plunger, when distally moved, causes the drive member to advance in a distal direction to force medication through an outlet, typically provided with an injection needle, at the distal end of the apparatus. An opening through one of the pinions accommodates the drive member to allow for a compact apparatus.

WO 2005/097233 A2 discloses a medication dispensing apparatus with a spring-driven locking feature. The apparatus includes a drive member movable in a distal direction within a housing, and a fluid container with a movable piston that is advanceable by the drive member when such drive member is moved distally by a driving means. The apparatus includes a latching element having a skid that is slidable along a surface of the drive member as the drive member passes distally during advancement. The drive member is structured and arranged with the skid so as to maintain a latching lip of the latching element against a spring force in a first position free of the driving means during dose preparing and injecting prior to a final dose administration. The skid-engaging surface shifts distally of the skid such that the skid passes beyond a proximal end of that surface upon administration of a final dose, whereby the latching lip is urged by the spring force from the first position to a second position to physically lock the driving means to prevent further dose preparing and injecting.

SUMMARY OF THE INVENTION

It is an object of the present invention to provide an alternative medication dispensing apparatus or injection device for dosing-up and delivering a defined dosage of a fluid product or respectively a number of defined dosages, i.e. a first, second and subsequent dosages up to a final dosage, wherein the defined dosages are of equal size, and to a method for operating the device. The medication dispensing apparatus or injection device prevents delivering a sub-dose being less than the defined dosage.

This object is solved by the subject matter of the independent claims. Advantageous embodiments follow from the dependent claims. In the following, the term "distal" is used to mean a direction towards the injection needle end of the injection device and the term "proximal" is used to mean a direction towards the end-cap end of the injection device.

The term "dosing-up" is used to refer to the process of preparing the apparatus or device prior to delivering or dispensing the dose. The term "dosed up" refers to the fully dosed up state and corresponding positions of the respective elements of the apparatus or device in that state, i.e. positions that allow an immediate subsequent dispensing operation.

A "dosing-up direction" refers to the direction of a movement, such as a longitudinal and/or rotational movement, of an element of the apparatus or device in the process of dosing-up. The term "dial-down direction" or "dispensing direction" refers to the direction of a movement of an element of the apparatus or device either when a user attempts to dial-down a not fully set dose or when the user performs a dispensing or delivering operation after having set by fully dosing-up a dosed state of the device or apparatus. Preferably the dosing-up direction is opposite to the dial-down direction or dispensing direction.

The pre-set dosage of a fluid product can be a dosage corresponding to the setting of one or more elements of the apparatus after having left a starting position corresponding to a zero dosage and when reaching an end position corresponding to the pre-set dosage. The movement of a respective element can for example be limited by projections or other appropriate elements blocking further movement of the respective element beyond a set position, for example below the initial position or above the pre-set dosage position.

The medication dispending apparatus or injection device for dosing-up and delivering a pre-set dosage of a fluid product comprises a housing, wherein the term "housing" refers to a housing per se and any elements fixedly coupled to the housing, such as the below-mentioned guiding sleeve being preferably non-relocatably coupled to the housing, so that the guiding sleeve is considered to be a housing element or housing. A dosing element, such as a dosage sleeve with or without an end cap coupled to the dosage sleeve, is movable relative to the housing and housing elements between a starting position corresponding to a zero dosage not allowing any dispensing operation and a dosed-up position corresponding to a pre-set dosage of a fluid product allowing thereafter to perform a dispensing operation for dispensing the pre-set dosage of the fluid product. The pre-set dosage can be a dosage set once before the medication dispensing apparatus is operated the first time and can remain a fixed preset dosage not being changeable when operating the device. The medication dispensing apparatus comprises a drive system comprising for example a rotating sleeve coupled to a plunger rod coupled to a flange which can exert a force on a stopper of a cartridge, wherein the drive system is coupled for example by threaded engagement to the dosing element and is operable to initiate or perform a dispensing operation. After the pre-set dosage has been fully set by appropriately moving the dosing element in a dosing-up direction, the dosing element can be operated in a dispensing direction and is coupled to the drive system in order to translate the dispensing operation of the user acting on the dosing element into a dispensing operation of the drive system effecting a dispensing operation, such as for example by shifting the stopper within a cartridge by a defined distance in order to displace or push the fluid product with an amount being the pre-set dosage out of the cartridge. The dosing element, such as a dosage sleeve, can for example be coupled by threaded engagement to a rotating element, such as a rotating sleeve so that, in case the dosage sleeve is for example rotationally fixed but axially shiftable with respect to the housing, the dosage sleeve can effect a rotational movement and/or a shift of the rotating sleeve with respect to the housing.

The rotating sleeve is according to one aspect of the invention not axially shiftable with respect to the housing, and according to another aspect of the invention, it is axially shiftable with respect to the housing by a pre-defined distance. The rotating sleeve can preferably be releasably coupled or unidirectionally coupled to a plunger rod in order to transfer a momentum or force onto the plunger rod during a dispensing operation, thus preferably effecting an advance movement of the plunger rod, wherein the coupling is preferably released when a dosing-up operation is performed, so that during the dosing-up process no force or momentum is transferred from the rotating sleeve to the plunger rod. The plunger rod itself can be in threaded engagement with the housing or a housing element, such that a rotational movement of the plunger rod effects an axial shift of the plunger rod.

The medication dispensing apparatus or injection device comprises a sub-dose preventing system preventing or blocking a dispensing operation of the drive system when the dosing element has not reached the dosed-up position corresponding to the pre-set dosage and is thus either in an initial or starting position or in an intermediate position between the starting position and the fully dosed-up position. The sub-dose preventing system allows or unblocks a dispensing operation of the drive system when and/or after the dosing element has reached the dosed-up position, so that the sub-dose preventing system can ensure that not less than the pre-set dosage is set by the dosing element before a dispensing operation can be started.

The sub-dose preventing system is operable to block a rotational movement of a drive element, such as a rotating sleeve, of the drive system, the rotational movement corresponding to a dispensing direction or a dial-down direction when preventing or blocking the dispensing operation of the drive system. A rotational movement of the drive element in the opposite dial-up or dosing-up direction is not blocked. Thus, the sub-dose preventing systems blocks a dispensing operation of the drive system before the fully dosed-up position has been reached by the dosing element.

The rotational movement of a drive element of the drive system which is blocked by the sub-dose preventing system is a rotational movement in a circumferential direction of the medication dispensing apparatus being a rotation about the longitudinal axis of the medication dispensing apparatus. Blocking the rotational movement of a drive element in the circumferential direction of the medication dispensing apparatus provides the advantage of easily and reliably constructing a drive element being able to be reliably blocked without having to add additional complexity to the medication dispensing apparatus, such as by introducing an element rotating for example about an axis extending oblique to the longitudinal axis of the medication dispensing apparatus. Thus, a medication dispensing apparatus according to the invention can be constructed in a compact manner while at the same time providing a reliable sub-dose preventing functionality.

The sub-dose preventing system can be a single element, such as a lock ring, or can be a combination of elements moveable with respect to each other. Preferably, the lock ring can either always be coupled to the housing or a housing element in a manner to allow a movement or rotation of the lock ring only in a single direction, such as a dosing-up direction, while blocking the movement or rotation in the opposite direction. According to an alternative embodiment, the lock ring can releasably be coupled to the housing or a housing element, such that the lock ring is for example decoupled from the housing element allowing rotational movement of the lock ring in any direction during a dial-up process and such that the lock ring is for example unidirectionally coupled to the housing allowing a movement or rotation only in the dosing-up direction and blocking a movement or rotation in the opposite direction when a dial-down operation is performed, thus blocking the dial-down or a desired dispensing operation. To effect the appropriate release and blocking of the drive system, an element of the drive system, such as a rotating sleeve, can for example be releasably and rotatively coupled to the lock ring, wherein the coupling takes place all time between a position of the rotating sleeve corresponding to an initial position and a dosed-up position where the preset dosage is set and can only be released after fully setting the pre-set dosage by appropriate movement or rotation of the rotating sleeve. This coupling to the preferably unidirectional movable lock ring ensures that in the process of dosing up no dial-down or dispensing operation can be performed.

Preferably, the sub-dose preventing system is operable to prevent a movement of the dosing element in a dial-down direction when preventing or blocking the dispensing operation of the drive system. In this case, the sub-dose preventing systems serves a double purpose, namely blocking the dispensing operation, such as blocking an advance movement of the plunger rod, and blocking a dial-down operation, such as a dial-down movement of the dosage sleeve. This can for example be achieved by the mentioned threaded engagement between the dosing element or dosage sleeve and a drive system element, such as a rotating sleeve. Preferably, the sub-dose preventing system, such as a lock ring, either is permanently or can alternatively releasably be coupled relative to the housing or a housing element, e.g. through a ratchet-means allowing a movement or rotation of the sub-dose preventing system or lock ring relative to the housing in a dosing-up direction and preventing a movement or rotation of itself and any element coupled to it in an opposing direction, such as a dial-down direction.

Preferably, the sub-dose preventing system comprises at least one coupling mechanism or ratchet tooth or ratchet toothing operable to engage or disengage with corresponding ratchet teeth of the housing or a housing element to prevent or block in the engaged state a rotation of the drive element in a dial-down direction, wherein the engagement or disengagement operation is performed by moving the at least one ratchet tooth relative to the sub-dose preventing system, which can be performed by providing a ratchet tooth on a latch or biased means connected to the sub-dose preventing system. Alternatively, the engagement or disengagement operation can be performed by moving the sub-dose preventing system or lock ring relative to the housing to thus couple or decouple the corresponding ratchet teeth by appropriately moving or shifting the sub-dose preventing system or lock ring.

A ratchet tooth or ratchet toothing of the sub-dose preventing system can preferably engage with corresponding ratchet teeth of the housing or a housing element either in an axial direction by facing the corresponding ratchet teeth in the axial direction or can alternatively engage corresponding ratchet teeth in a radial direction of the medication dispensing apparatus.

Preferably, the sub-dose preventing system is a tubular member or sleeve-shaped, such as a lock ring, which can comprise coupling means for releasably or permanently coupling with the housing and/or the drive system.

The tubular member of the sub-dose preventing system preferably comprises a coupling mechanism or coupling teeth on a surface opposing preferably in a radial direction a corresponding coupling mechanism or teeth of a tubular member or rotating sleeve of the drive system to releasably rotatively couple the tubular member of the sub-dose preventing system with the tubular member or rotating sleeve of the drive system.

The rotating sleeve of the drive system can preferably either be disposed on the radial inner side of the sub-dose preventing system or on the radial outer side thereof.

The sub-dose preventing system can preferably be movable in an axial direction of the medication dispensing apparatus to open or release a coupling between the sub-dose preventing system or lock ring and the housing or a housing element, as mentioned above, when the dosing element is operated or moved in a dosing-up direction and is movable in the opposite direction to couple with a housing or a housing element to block rotation when the dosing element is operated or moved in a dial-down direction.

The drive system preferably comprises a plunger rod comprising at least one groove or cam extending along the axial direction of the plunger rod, wherein in a circumferential direction of the plunger rod one, two, three or more axial extending grooves or cams can be provided. The circumferential distance between two neighboring grooves or cams can be used to set or define the pre-set dosage of a fluid product. Preferably, in case two or more axially extending grooves or cams are provided in the circumferential direction on the plunger rod, the circumferential distance between two adjacent grooves or rods is equal. In case of using for example four axially extending grooves, these are displaced by 90° in circumferential direction. The grooves or cams are able to cooperate with at least one coupling or engaging element of a drive element, being for example an arm moveable in radial direction, so that the engaging element of the drive element is for example in a radial outer or release position or disengaged position allowing a movement or rotation of the drive element with respect to the plunger rod at least in a dosing-up direction, when the engaging element is not coupled to a groove or cam. Preferably, the plunger rod is rotatively coupled to the housing by appropriate coupling means of the housing, such as a thread. Preferably, after having set the pre-set dosage, the engaging element of the drive element traveled from one groove or cam to an adjacent groove or cam in a dosing-up direction in order to engage therewith, thus performing for example a radial inward movement of the engaging element to rotatively couple with the plunger rod, preferably at least for being able to effect a dispensing direction, so that a rotational movement of the drive element can be transmitted to the plunger rod, at least in a dispensing direction.

Preferably a coupling mechanism such as coupling teeth are provided on an engaging element being for example the same engaging element as mentioned above being connected to the drive element, which coupling mechanism is for example radially movable to an engaging position, such as a radial outer position, engaging with a corresponding coupling mechanism or teeth of the sub-dose preventing system or lock ring being for example provided on an inner circumferential surface of the lock ring, in order to rotatively couple the drive element therewith. This rotative coupling takes place when the engaging element is out of engagement of groove or cam of plunger rod, being moved out to the radial outer position. The rotative coupling between drive element and sub-dose preventing system or lock ring can be released, when the engaging element is shifted to the opposite, e.g. radial inner direction to thus decouple the drive element from the sub-dose preventing system and to couple again the drive element with the plunger rod. Preferably, the drive element comprises an engaging element which, once out of engagement of a groove or cam of a plunger rod and moved a small distance in a dial-up direction, cannot travel back the dial-up movement but can only move to the adjacent groove or cam of the plunger rod.

The coupling or decoupling operation of the engaging element of the drive element to either the plunger rod or to the sub-dose preventing system or lock ring can be as described above or can be in any other direction, such as the opposite direction in case the plunger rod is for example a hollow plunger rod and provided on the outer side of the drive element, wherein the sub-dose preventing system or lock ring is on the inner side of the drive element.

The dosing element is preferably shiftable in an axial direction of the housing, such as in the proximal direction or dosing-up direction when being in the process of setting the dosage and in the opposite direction when performing a dispensing operation.

According to a further aspect, a method is provided for preventing a dispensing operation of a medication dispensing apparatus as described above, wherein when the dosing element was moved in a dial-up direction to a position corresponding to less than a pre-set dosage, such as for example pulling the dosage sleeve not fully out of the housing, and in this state an operation or force is applied to the dosage element acting in the opposite or dial down direction, the dosing element is coupled directly or indirectly, for example by being coupled to a rotating sleeve, to the sub-dose preventing system preventing or blocking a rotation of a drive element, such as the rotating sleeve, in a circumferential direction, or blocking a movement of the dosing element in the dial-down direction or blocking a movement of the plunger rod, at least in a dispensing direction.

In the following, preferred embodiments are described.

In order to dose-up a defined dosage of the fluid product, the rotating sleeve can be rotated relative to the guiding sleeve until the rotational movement is restricted by a first abutment contact between the rotating sleeve and the guiding sleeve. To this end, the rotating sleeve can be rotated in a first rotational direction. For dosing-up the fluid product, the dosage sleeve can be drawn out of the injection device axially, whereas for administering the fluid product, the dosage sleeve can be pushed into the injection device axially. For administering the fluid product, the rotating sleeve can therefore be rotated in a second rotational direction until the rotational movement is restricted by a second abutment contact between the rotating sleeve and the guiding sleeve. The first and second abutment contact between the rotating sleeve and the guiding sleeve can be formed by providing the rotating sleeve with a projection which protrudes radially outwards and can be rotatively moved back and forth between two projections which are provided on the guiding sleeve and protrude radially inwards. Alternatively, the rotating sleeve comprises two projections which protrude radially outwards and can be rotatively moved back and forth between corresponding projections which are disposed on the guiding sleeve and protrude radially inwards.

The engaging element of the rotating sleeve and the engaging element of the guiding sleeve can co-operate with the toothing of the plunger rod such that the plunger rod can be allowed to rotate in one rotational direction and blocked against rotating in the opposite rotational direction. For administering the fluid product from the injection device, the plunger rod is allowed to rotate, whereas for dosing-up the fluid product, it is blocked against rotating. The plunger rod can be connected to the guiding sleeve or alternatively to a housing of the injection device by means of a threaded connection. The guiding sleeve can be connected to the housing such that it is axially fixed and rotationally fixed, or alternatively can be embodied integrally with the housing.

The engaging elements of the rotating sleeve and guiding sleeve can be embodied as elastic spring arms, wherein the engaging elements can be disposed on the corresponding sleeves in the circumferential direction. The engaging elements of the rotating sleeve and guiding sleeve can comprise a tip which exhibits one steep and one flat flank. These tips can elastically engage with the toothing of the plunger rod by means of spring arms. The mechanism by which the engaging elements of the rotating sleeve and guiding sleeve engage with the toothing of the plunger rod can be embodied as a ratchet mechanism. To this end, the plunger rod can comprise a number of longitudinal notches or longitudinal grooves in the longitudinal direction which form a tooth, preferably a number of teeth, with one or more tooth gaps. The longitudinal notch or longitudinal groove or tooth or tooth gap comprises one steep and one flat flank.

The defined dosage can be defined on the one hand by the rotational positions which are defined between the first and second abutment contact between the abutments of the rotating sleeve and guiding sleeve and on the other hand by the thread pitch between the rotating sleeve and the dosage sleeve and/or axial path of the dosage sleeve. Alternatively or additionally, the axial path of the dosage sleeve can be restricted by axial abutments and counter-abutments. To this end, the dosage sleeve can comprise two axially spaced abutments.

The injection device can provide for the drawing-up movement of the dosage sleeve and/or the delivery movement of the plunger rod to be translated up or down. To this end, the thread pitch of the threaded engagement between the guiding sleeve or housing and the plunger rod and the thread pitch of the threaded engagement between the dosage sleeve and the rotating sleeve can be different. Preferably, the thread pitch of the threaded engagement between the dosage sleeve and the rotating sleeve is greater than the thread pitch of the threaded engagement between the guiding sleeve or housing and the plunger rod. Alternatively, the thread pitch of the threaded engagement between the guiding sleeve or housing and the plunger rod can be greater than or equal to the thread pitch of the threaded engagement between the dosage sleeve and the rotating sleeve. Preferably, the rotating sleeve and the guiding sleeve comprise an engaging element each, and the plunger rod comprises four longitudinal notches or longitudinal grooves and/or four longitudinal teeth with four tooth gaps which are arranged such that they are offset by about 90 degrees with respect to each other in the circumferential direction. Alternatively, the rotating sleeve comprises two engaging elements which are arranged on the rotating sleeve such that they are offset by about 180 degrees with respect to each other in the circumferential direction, and the guiding sleeve comprises two engaging elements which are disposed on the guiding sleeve, likewise such that they are offset by about 180 degrees with respect to each other in the circumferential direction. Alternatively, four engaging elements can be respectively provided on the rotating sleeve or guiding sleeve, which are arranged such that they are offset by about 90 degrees with respect to each other in the circumferential direction.

Alternatively, the number of engaging elements disposed on the rotating sleeve and the guiding sleeve and the number of longitudinal notches or longitudinal grooves and/or longitudinal teeth or tooth gaps provided on the plunger rod can be the same.

The injection device preferably comprises two abutment contacts between the rotating sleeve and guiding sleeve, wherein the abutment contacts are arranged such that they are offset in the circumferential direction and the distance between the two abutments approximately corresponds to the distance between two adjacent latching positions in which the engaging element of the rotating sleeve and/or guiding sleeve engages with the longitudinal notch or longitudinal groove or tooth gap of the plunger rod.

The engaging elements of the rotating sleeve and guiding sleeve and the toothing of the plunger rod can be embodied such that one or more clicking sounds can be generated when dosing-up and when delivering the fluid product.

Due to the threaded connection between the dosage sleeve, which can be mounted in the housing of the injection device such that it is rotationally fixed but can be moved axially, and the rotating sleeve which can be provided in the housing of the injection device such that it is axially fixed but can be rotated, the rotating sleeve can move in one rotational direction, the dosing-up direction, when dosing up the fluid product and in one rotational direction, the delivery direction, when delivering the fluid product.

When dosing-up the fluid product, the plunger rod can be held such that it is axially fixed and rotationally fixed relative to the housing of the injection device with the aid of the engagement between the engaging element of the guiding sleeve and the toothing of the plunger rod. To this end, a steep flank of the tip of the engaging element of the guiding sleeve and a steep flank of the longitudinal notch or longitudinal groove or tooth or tooth gap pass into abutment contact. When dosing-up the fluid product, the engaging element of the rotating sleeve can also pass out of engagement with the toothing of the plunger rod, wherein a flat flank of the tip of the engaging element of the rotating sleeve slides over a flat flank of the longitudinal notch or longitudinal groove or tooth or tooth gap of the plunger rod and passes into the next longitudinal notch or longitudinal groove or tooth gap of the plunger rod.

When delivering the fluid product, the rotating sleeve can transmit the rotational movement onto the plunger rod due to an abutment between a steep flank of the tip of the engaging element of the rotating sleeve and a steep flank of the longitudinal notch or longitudinal groove or tooth of the plunger rod, wherein a flat flank of the tip of the engaging element of the guiding sleeve slides over a flat flank of the longitudinal notch or longitudinal groove or tooth or tooth gap of the plunger rod. When delivering the defined dosage, the plunger rod can be screwed in the distal direction due to the threaded connection between the plunger rod and the guiding sleeve or alternatively the housing, wherein the engaging element, in particular the tip or a part of the tip of the rotating sleeve, slides axially along the longitudinal notch or longitudinal groove of the plunger rod. The plunger rod is moved axially in the distal direction relative to the housing of the injection device and, via a flange, pushes a stopper in the distal direction. The flange can be fastened to the distal end of the plunger rod such that it is axially fixed but can preferably be rotated. The stopper in a cartridge can press the fluid product out via an injection needle which is fastened to the cartridge or to a cartridge holder which accommodates the cartridge.

In order to protect the cartridge or the cartridge holder which accommodates the cartridge, the injection device can comprise a pen cap. The pen cap can be connected to the housing of the injection device such that it is axially fixed and preferably rotationally fixed. The pen cap can be removed from the injection device in order to dispose an injection needle on the cartridge before the injection device is used, by enabling a cannula of the injection needle to pierce a septum of the cartridge in order to form a fluid connection between the injection needle and the cartridge The injection device can feature an end cap which can be disposed on the proximal end of the dosage sleeve such that it is axially fixed and preferably rotationally fixed. The end cap can be formed integrally with the dosage sleeve.

The injection device can also feature a mechanism which can prevent another dosage from being set once the final dosage has been delivered.

To this end, the rotating sleeve of the injection device can comprise an abutment which pushes against an abutment provided on the plunger rod. An axial and/or radial abutment contact between the rotating sleeve and the plunger rod can thus prevent another dosage from being set or drawn up once the final dosage has been delivered. Preferably, two abutments can be provided on the rotating sleeve and can come into abutment contact with two corresponding abutments disposed on the plunger rod and so prevent a rotational movement of the rotating sleeve in the dosing-up direction.

In one example embodiment, the dosage sleeve can be arranged between the rotating sleeve and the guiding sleeve. In another example embodiment, the guiding sleeve and the dosage sleeve can be arranged coaxially in the injection device. The threaded connection between the rotating sleeve and the dosage sleeve can be embodied as a single-flight or multiple-flight threaded connection or as segments of a threaded connection.

The injection device can also comprise an indicating device which can indicate the initial position, the drawn-up position and/or the delivered position of dosage sleeve or setting button. The indicating device can be embodied as a visual, acoustic and/or tactile indicator. The visual indicating device can comprise a marking and/or a symbol and/or an indicative number.

To this end, the injection device can comprise an indicating sleeve comprising an indicating device. The indicating sleeve is preferably connected to the dosage sleeve integrally. Alternatively, the dosage sleeve can comprise an indicating device. The dosage sleeve can also comprise a visual indicating device in the form of a print and/or sticker.

BRIEF DESCRIPTION OF THE DRAWINGS

FIGS. 1A-1D is an injection device or dispensing apparatus according to a first embodiment in an initial state before a dosing-up operation is performed;

FIGS. 2A-2D is the injection device of FIGS. 1A-1D during a dosing-up operation; and FIGS. 3A-3D is the injection device being fully dosed-up until the pre-set dosage.

FIG. 4A is an exploded view of the guiding sleeve, lock ring and rotating sleeve according to a second embodiment;

FIG. 4B is a cross-sectional view of the elements shown in FIG. 4A;

FIG. 4D is an cross-sectional view of the elements shown in FIG. 4C.

DETAILED DESCRIPTION

Figure 4C:
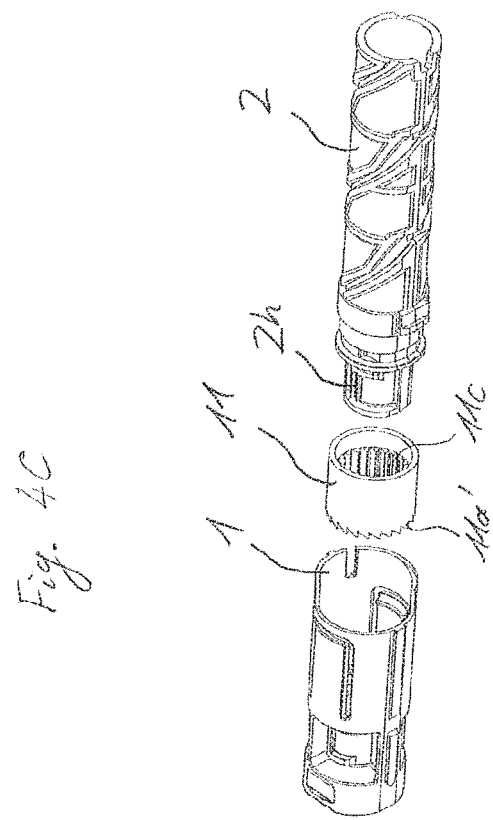
FIG. 4C is an exploded view of the guiding sleeve, lock ring and rotating sleeve according to the second embodiment.

FIGS. 1A to 1D show a first embodiment of an injection device or dispensing apparatus in an unloaded state, i.e. no dose has been dialed-up. The injection device comprises a cartridge holder 8 which can accommodate a cartridge 10, wherein the cartridge holder 8 is connected, axially fixed, to a distal guiding sleeve cavity 1*i* of a guiding sleeve 1 being connected to a housing 6 by receiving a cartridge holder protrusion 8*a* in the guiding sleeve cavity 1*i*. A cartridge holder stay 8*b* for a rotationally fixed connection to the housing 6 or guiding sleeve 1 via a corresponding guiding sleeve groove 1*l* is also provided on the cartridge holder 8. A cartridge holder abutment 8*c* can axially abut a distal guiding sleeve edge 1*j* of the guiding sleeve 1. A cartridge holder cavity 8*d* in the cartridge holder 8 serves to indicate the relative position of a stopper 10*a* which can be axially moved in the cartridge 10. The cartridge holder cavity 8*d* is interrupted by a cartridge holder transverse stay 8*e*, wherein the cartridge holder cavity 8*d* is divided into two parts. If the stopper 10*a* is situated in the more distally arranged part of the cartridge holder cavity 8*d*, the user can tell for example that the final dosage has been delivered from the injection device and a new dosage cannot be drawn up. A needle connecting element 8*f* is provided on the distal end of the cartridge holder 8 and is provided for detachably fastening an injection needle 9. The injection device also comprises a pen cap (not shown) which can be connected to the cartridge holder 8 via a detachable connection. To this end, the cartridge holder 8 comprises a cartridge holder projection 8*g* which can latch into an annular groove of the pen cap. The pen cap can preferably comprise a pen cap clip. The annular groove of the pen cap preferably comprises a recess, such that the pen cap can be arranged such that it is rotationally fixed relative to the cartridge holder 8.

The injection device also comprises a guiding sleeve 1 which is connected, such that it is axially fixed and rotationally fixed, to the housing 6 of the injection device via a positive fit, and can thus be considered as being a housing element. To this end, the housing 6 comprises a housing window 6*d*. A guiding sleeve stay 1*f* is also arranged on the guiding sleeve 1 and forms a rotationally fixed connection in the housing 6 with a groove. The guiding sleeve 1 comprises an engaging element 1*a* which can co-operate with a toothing of the plunger rod 3.

The injection device also comprises a rotating sleeve 2 which is connected, such that it is axially fixed but can be rotated, to the guiding sleeve 1. To this end, the rotating sleeve 2 comprises a rotating sleeve annular stay 2*c* which can axially abut the guiding sleeve holding arm 1*b*, preferably two guiding sleeve holding arms 1*b*, wherein the rotating sleeve edge 2*d* can also form an axial abutment contact with a guiding sleeve facing side 1*c* of the guiding sleeve 1. The rotating sleeve 2 likewise comprises an engaging element 2*a* which can co-operate with a toothing of the plunger rod 3.

The toothing of the plunger rod 3 comprises a groove or tooth 3*a*, preferably a number of teeth, and preferably four teeth. The plunger rod 3 also comprises an outer thread 3*b* which forms a threaded connection with an inner thread 1*g* of the guiding sleeve 1. The mechanism by which the engaging elements 2*a*, 1*a* of the rotating sleeve 2 and guiding sleeve 1 engage with the toothing 3*a* of the plunger rod 3 is embodied as a ratchet mechanism. The engaging elements 2*a*, 1*a* of the rotating sleeve 2 and guiding sleeve 1 co-operate with the toothing of the plunger rod 3 such that a clicking sound is generated when dosing-up the defined dosage and when delivering the defined dosage.

In order to prevent another dosage from being set once the final dosage has been delivered, the rotating sleeve 2 can comprise a rotating sleeve abutment which can come into abutment contact with a plunger rod abutment provided on the plunger rod 3.

The injection device also comprises a dosage sleeve 4. The dosage sleeve 4 is mounted, via a dosage sleeve stay together with a housing groove (not shown) of the housing 6, such that it is rotationally fixed but can be moved axially relative to the housing 6 of the injection device. The user can move the dosage sleeve 4 axially back and forth with the aid of an end cap 5 arranged on the proximal end of the dosage sleeve 4. For indicating the individual dosing movements, the dosage sleeve 4 preferably comprises an indicator 4*c*. The end cap 5 which is connected, axially fixed, to a dosage sleeve annular stay 4*e* of the dosage sleeve 4 via an end cap groove 5*a* can also be disposed on the proximal end of the dosage sleeve 4. The dosage sleeve 4 is connected to the rotating sleeve 2 via a threaded connection. The inner side of the dosage sleeve 4 comprises a dosage sleeve thread 4*b* which is in engagement with the rotating sleeve thread 2*b* on the outer side of the rotating sleeve 2.

A lock ring 11 comprises on the rear or proximal side an abutment side 11*d* being in contact with abutment side 2*g* of the rotating sleeve 2 and comprises on the opposing front or proximal side a latch arm 11*b* having a ratchet tooth 11*a* on its end, the ratchet tooth 11*a* pointing in the axial distal direction of the lock ring 11. The ratchet tooth 11*a* engages a ratchet toothing 1*k* of the guiding sleeve 1 being on the proximal side of guiding sleeve 1 to thus provide a ratchet mechanism 1*k*, 11*a* allowing rotation of the lock ring 11 with respect to guiding sleeve 1 only in one direction (clockwise in FIG. 1D) and preventing a rotational movement of the lock ring 11 in the opposing direction (counter clockwise direction in FIG. 1D). The lock ring 11 can thus not be shifted in the axial direction with respect to the housing 6 or the guiding sleeve 1 and can perform a rotational movement in one direction only. Lock ring 11 comprises on its radial inner surface a coupling toothing 11*c* being axially offset with respect to latch arm 11*b* and being provided along 360° of the circular inner surface of lock ring 11.

FIG. 1A shows a longitudinal sectional view of the first embodiment of the injection device, with a dosage sleeve 4 in an initial position. The dosage sleeve 4, which is mounted such that it can be axially moved but is rotationally fixed in the housing 6, is inserted in the injection apparatus, wherein the indicator 4*c* which is disposed on the dosage sleeve 4 can be seen through the housing window 6*d* and indicates to the user that the injection device is in the initial position. The dosage sleeve 4 is in threaded engagement with the rotating sleeve thread 2*b* of the rotating sleeve 2 via the dosage sleeve thread 4*b*.

Turning to FIGS. 1A to 1D, the rotating sleeve 2 at a projection (not shown) of the rotating sleeve 2 protrudes radially outwards and is situated in abutment contact with the guiding sleeve 1 at a first projection (not shown) of the guiding sleeve 1 which protrudes axially in the proximal direction. Tips 2*a*' which are disposed on engaging elements 2*a* of the rotating sleeve 2 are in engagement with the grooves or toothing 3*a* of the plunger rod 3. To this end, tips 2*a*' of the engaging elements 2*a* of the rotating sleeve 2 interlock with grooves or tooth gaps 3*a* of the plunger rod 3, namely between a steep flank 3*a*' and a flat flank 3*a*" of the groove 3*a* of plunger rod 3. A tip provided on the engaging element 1*a* of the guiding sleeve 1 is likewise in engagement with the toothing or grooves 3*a* of the plunger rod 3. To this end, the tip of the engaging element 1*a* of the guiding sleeve 1 likewise interlocks with a tooth gap or groove 3*a* of the plunger rod 3. The tip of the engaging element 1*a* of the guiding sleeve 1 is situated between a steep flank 3*a*' and a flat flank 3*a*" of the plunger rod 3.

Arranged on the radial outer side of engaging element 2a of rotating sleeve 2 is a coupling toothing 2h which is in the initial position shown in FIG. 1C out of engagement with corresponding coupling toothing 11c of lock ring 11 due to tip 2a' of flexible engaging element 2a of rotating sleeve 2 being in engagement with tooth or groove 3a of plunger rod 3.

FIGS. 2A to 2D show views of the first embodiment of the injection device, with the dosage sleeve 4 in a draw-up position. In order to set or draw up a dosage, the user draws the end cap 5 in the proximal direction, wherein the dosage sleeve 4 connected to the end cap 5 is shifted axially in the proximal direction. Due to the threaded engagement 2b, 4b between the dosage sleeve 4 and the rotating sleeve 2, the rotating sleeve 2 rotates in a first rotational direction until in the fully dosed-up position shown in FIGS. 3A-3D. In this position, the projection of the rotating sleeve 2 passes into abutment contact with the guiding sleeve 1 at a second projection (not shown) of the guiding sleeve 1 which protrudes axially in the proximal direction, wherein the flat flanks 2a''' of the tips 2a' of the engaging elements 2a of the rotating sleeve 2 slide over the flat flanks 3a'' of the grooves or teeth 3a of the plunger rod 3 and thereby the engaging elements 2a are located in between two grooves 3a on the outer side of plunger rod 3, thus shifting or pressing engaging elements 2a radially outwards, so that coupling toothing 2h on the radial outer side of the engaging elements 2a engages with coupling toothing 11c on the radial inner side of lock ring 11. Since lock ring 11 is held by ratchet coupling 11a, 1k at guiding sleeve 1 against a rotation in the dial-down direction while allowing rotation in a dial-up direction, rotating sleeve 2 being in this dial-up state rotationally coupled to lock ring 11 can also only be rotated in a dial-up direction while being blocked with respect to a rotation in the dial-down direction.

A steep flank 1a'' of the tip 1a' of the engaging element 1a of the guiding sleeve 1 is in abutment contact with the steep flank 3a' of the groove 3a of the plunger rod 3, such that the plunger rod 3 is held rotatively fixed with respect to guiding sleeve 1 and housing 6. The indicator 4c which is disposed on the dosage sleeve 4 indicates to the user, through the housing window 6d, that the injection device is in a draw-up position.

FIGS. 3A to 3D show views of the first embodiment of the injection device with the dosage sleeve 4 in the fully drawn-up position. End cap 5 has been drawn by the user in the proximal direction to the fully dosed-up position, shifting the dosage sleeve 4 axially in the proximal direction to the fully dosed-up position. Due to the threaded engagement 2b, 4b between the dosage sleeve 4 and the rotating sleeve 2, the rotating sleeve 2 rotates in the first rotational direction until the projection of the rotating sleeve 2 comes in abutment contact with the guiding sleeve at the second projection. In the described first embodiment, this corresponds to a 90 degree turn in the counter clockwise direction, as can be seen by the 90 degree turn of rotating sleeve 2 shown in FIG. 3C when compared to FIG. 1C showing the initial state. In this position, engaging element 2a which may be biased in a radial inward direction, can move in the radial inward direction, since tip 2a' of the engaging element 2a can enter the next groove 3a of plunger road 3, thus, causing an opening or disengagement between coupling toothing 2h of rotating sleeve 2 and coupling toothing 11c of lock ring 11, which releases the rotative coupling between rotating sleeve 2 and lock ring 11. Thus, rotating sleeve 2 is now free to rotate in a dispensing direction opposing the dial-up direction (clockwise in the embodiment shown in FIG. 3C). Due to the coupling 2a', 3a, this rotation of rotating sleeve 2 will cause a rotation of plunger rod 3.

The drawing-up movement of the dosage sleeve 4 and the delivery movement of the plunger rod 3 can be the same or alternatively are translated up. In this case, the thread pitch of the threaded connection 4b, 2b between the dosage sleeve 4 and the rotating sleeve 2 is greater than the thread pitch of the threaded connection 3b, 1g between the plunger rod 3 and the guiding sleeve 1. In order to deliver a defined dosage, the user presses the end cap 5 in the distal direction, wherein the dosage sleeve 4 is shifted axially in the distal direction. The rotating sleeve 2 rotates in the rotational direction opposite to the first rotational direction until the projection of the rotating sleeve 2 passes into abutment contact with the guiding sleeve 1 at the first projection. The steep flank 2a'' of the tip 2a' of the engaging element 2a of the rotating sleeve 2 is in abutment contact with the steep flank 3a' of the tooth 3a of the plunger rod 3 and transmits a torque onto the plunger rod 3. This screws the plunger rod 3 in the distal direction due to the threaded connection between the inner thread 1g of the guiding sleeve 1 and the outer thread 3b of the plunger rod 3, wherein the tip 2a' of the engaging element 2a of the rotating sleeve 2 slides axially along the groove gap 3a''' of the plunger rod 3. The flat flank 1a''' of the tip 1a' of the guiding sleeve 1 slides over the flat flank 3a'' of the tooth 3a of the plunger rod 3, wherein a stopper 10a which is accommodated by a cartridge 10 is pushed in the distal direction via a flange 7 which is disposed, axially fixed, on the plunger rod 3. The stopper 10a can press the fluid product out via an injection needle 9 which is fastened to the cartridge holder 8.

The above described procedure of dialing-up and dispensing a dose can thereafter be repeatedly performed.

Once the final dosage has been delivered from the injection device, the stopper 10a is situated in the distally arranged part of the cartridge holder cavity 8d, which is divided into two parts by the cartridge holder transverse stay 8e. The user can thus tell that the final dosage has been delivered from the injection device and a new dosage cannot be drawn up. Two rotating sleeve abutments of the rotating sleeve 2 can then be in abutment contact with two corresponding plunger rod abutments of the plunger rod 3 so that no further dosage can be drawn up via the dosage sleeve 4, since the rotating sleeve 2 is blocked against rotating.

FIGS. 4A to 4D show a second embodiment of an injection device differing from the first embodiment with respect to the guiding sleeve 1, the lock ring 11 and the rotation sleeve 2. The remaining above described elements of the injection device can function in the same manner as described above.

According to the second embodiment, the rotating sleeve 2 being coupled to dosage sleeve 4 by means of threaded engagement 2b, 4b is not held in an axial fixed position by means of guiding sleeves stay 1f, which is offset proximally in the axial direction, thus allowing lock ring 11 to be axially shifted. Lock ring 11 comprises on its distal side (left side in FIGS. 4A to 4D) ratchet teeth 11a' arranged on the radial outer position on the distal facing side of lock ring 11 to engage or disengage depending on the axial position of lock ring 11 with respect to guiding sleeve 1 with ratchet toothing 1k' arranged on a side of guiding sleeve 1 facing ratchet teeth 11a' of lock ring 11. Thus, lock ring 11 is freely rotatable with respect to guiding sleeve 1 when being shifted in the proximal direction, so that coupling 11a', 1k' is opened. In case lock ring 11 is shifted in the distal direction so that coupling 11a', 1k' is closed, lock ring 11 can only be rotated with respect to guiding sleeve 1 in a first direction corresponding to a dial-up direction or rotation, wherein rotation in the counter direction corresponding to a dial-down direction is blocked.

The de-coupling or axial shifting of lock ring 11 is effected by the user pulling end cap 5 and dosage sleeve 4 out of the injection device in the proximal direction, which causes rotating sleeve 2 to also be shifted in the proximal direction due to threaded coupling 2b, 4b, thus allowing lock ring 11 to be de-coupled from guiding sleeve 1 by allowing lock ring 11 to be shifted in the proximal direction to open coupling 11a', 1k'.

If end cap 5 and dosage sleeve 4 are pressed into the injection device, dosage sleeve 4 is moved into the distal direction through threaded engagement 2b, 4b thus pressing lock ring 11 in the distal direction to close coupling 11a', 1k'.

Lock ring 11 comprises on its inner circumferential side a coupling toothing 11c, as described above, which can engage or disengage with corresponding coupling toothing 2h of rotating sleeve 2 in the manner described above.

A common concept of the above described two embodiments is that lock ring 11 allows a dial-up operation or rotation and prevents a dial-down operation or rotation of rotating sleeve 2 when the pre-set dose has not been fully dialed-up. Only after the pre-set dose was fully dialed up by rotating sleeve 2 a predefined amount being 90 degrees in the described embodiments, rotation sleeve 2 is de-coupled from lock ring 11 and is then free to be moved or rotated in a counter-dial-up direction being a dispensing direction, thus ensuring that a dispensing operation can only be performed after a full predefined dial-up operation has been performed.

Although certain embodiments of the present disclosure are described herein with reference to the examples in the accompanying figures, it would be apparent to those skilled in the art that several modifications to the described embodiments, as well as other embodiments of the present invention are possible without departing from the spirit and scope of the present disclosure.

What is claimed is:

1. A medication dispensing apparatus for dosing-up and delivering a pre-set dosage of a fluid product, comprising:
    a housing;
    a dosing element moveable relative to the housing between a starting position and a dosed-up position;
    a drive system coupled to the dosing element, the drive system operable to initiate or perform a dispensing operation; and
    a sub-dose preventing system for preventing or blocking the dispensing operation of the drive system when the dosing element has not reached the dosed-up position, and for allowing or unblocking the dispensing operation of the drive system when or after the dosing element has reached the dosed-up position,
        wherein the sub-dose preventing system is operable to block a rotational movement in a circumferential direction of the medication dispensing apparatus of a drive element of the drive system corresponding to a dial-down direction when preventing or blocking the dispensing operation of the drive system,
        wherein the drive system comprises a plunger rod, the plunger rod comprising at least one coupling element configured to cooperate with at least one coupling or engaging element of the drive element, wherein the at least one coupling or engaging element of the drive element is in a release position allowing movement or rotation of the drive element with respect to the plunger rod at least in a dosing-up direction when the at least one coupling or engaging element of the drive element is not coupled to the at least one coupling element of the plunger rod, and effecting a rotational coupling with the plunger rod at least in a dispensing direction when the at least one coupling or engaging element of the drive element is coupled to the at least one coupling element of the plunger rod, and
        wherein a coupling mechanism is provided on the at least one coupling or engaging element of the drive element which is movable to an engaging position for engaging with a coupling mechanism of the sub-dose preventing system to rotatively couple the drive element therewith when the at least one coupling or engaging element of the drive element is out of an engagement with the coupling element of the plunger rod, and in a disengagement position, the drive element is decoupled from the sub-dose preventing system when the at least one coupling or engaging element of the drive element is in an engagement with the coupling element of the plunger rod.

2. The medication dispensing apparatus of claim 1, wherein the sub-dose preventing system is operable to prevent a movement of the dosing element in the dial-down direction when preventing or blocking the dispensing operation of the drive system.

3. The medication dispensing apparatus of claim 1, wherein the sub-dose preventing system is or can be coupled relative to the housing through a coupling mechanism or ratchet-means allowing a movement or rotation of the sub-dose preventing system relative to the housing in the dosing-up direction and preventing a movement or rotation in the dial-down direction.

4. The medication dispensing apparatus of claim 1, wherein the sub-dose preventing system comprises at least one ratchet tooth operable to engage or disengage with corresponding ratchet teeth of the housing or a housing element thereof to prevent or block in an engaged state a rotation of the drive element in the dial-down direction, wherein an engagement or a disengagement operation is performed by moving the at least one ratchet tooth relative to the sub-dose preventing system or by moving the sub-dose preventing system relative to the housing.

5. The medication dispensing apparatus of claim 4, wherein in the engagement operation, the at least one ratchet tooth engages with the ratchet teeth of the housing or housing element thereof in an axial direction or a radial direction of the medication dispensing apparatus.

6. The medication dispensing apparatus of claim 1, wherein the sub-dose preventing system comprises a tubular member or is sleeve-shaped.

7. The medication dispensing apparatus of claim 6, wherein the sub-dose preventing system comprises the tubular member, and the tubular member comprises a coupling mechanism or coupling teeth on a surface opposing a coupling mechanism or coupling teeth of a tubular member or a rotating sleeve of the drive system to releasably rotatively couple the tubular member of the sub-dose preventing system with the tubular member or the rotating sleeve of the drive system.

8. The medication dispensing apparatus of claim 7, wherein the rotating sleeve of the drive system is disposed on a radial inner side or on a radial outer side of the sub-dose preventing system.

9. The medication dispensing apparatus of claim 1, wherein the sub-dose preventing system is moveable in an axial direction of the medication dispensing apparatus to open or release a coupling between the sub-dose preventing system and the housing or a housing element thereof when the dosing element is operated or moved in the dosing-up direction and is moveable in the opposite direction to couple with the housing or a housing element thereof to block rotation when the dosing element is operated or moved in the dial-down direction.

10. The medication dispensing apparatus of claim 1, wherein the at least one coupling element of the plunger rod is configured as a groove or a tooth.

11. The medication dispensing apparatus of claim 1, wherein the at least one coupling element of the plunger rod is configured as a plurality of coupling elements axially extending in the circumferential direction.

12. The medication dispensing apparatus of claim 1, wherein the coupling mechanism of the drive element or the sub-dose preventing system is configured as coupling teeth.

13. The medication dispensing apparatus of claim 1, wherein the plunger rod comprises a thread coupled to the housing or a housing element thereof to effect an axial movement of the plunger rod with respect to the housing when the plunger rod rotates.

14. The medication dispensing apparatus of claim 1, wherein the dosing element is shiftable in an axial direction of the housing and cannot be rotated with respect to the housing.

15. The medication dispensing apparatus of claim 1, wherein the drive element of the drive system is arranged on a radial outer side of the plunger rod and on a radial inner side of the sub-dose preventing system.

16. The medication dispensing apparatus of claim 1, wherein when movement of the dosing element in the dosing-up direction to a position corresponds to less than a pre-set dosage and an operation or force is applied to the dosing element in the dial-down direction, the dosing element is coupled to the sub-dose preventing system to prevent or block a rotation of the drive element and/or a movement of the dosing element and/or a movement of the plunger rod in the circumferential direction of the medication dispensing apparatus.

17. A method for preventing a dispensing operation of a medication dispensing apparatus using the medication dispensing apparatus of claim 1, wherein when the dosing element is moved in the dosing-up direction to a position corresponding to less than a pre-set dosage and an operation or force is applied to the dosing element in the dial-down direction, the dosing element is coupled to the sub-dose preventing system to prevent or block a rotation of the drive element and/or a movement of the dosing element and/or a movement of the plunger rod in the circumferential direction of the medication dispensing apparatus.

* * * * *